United States Patent
Hosking et al.

(10) Patent No.: US 12,415,010 B2
(45) Date of Patent: Sep. 16, 2025

(54) ROOM AIR PURIFICATION UNIT

(71) Applicant: Price Industries, Inc., Suwanee, GA (US)

(72) Inventors: Nolan Hosking, Alpharetta, GA (US); Michael Holliday, Auburn, GA (US); Mark Mahon, Winnipeg (CA); Chris Hildebrand, Winnipeg (CA); Tim Ko, Atlanta, GA (US); Elizabeth Turner, Lawrenceville, GA (US)

(73) Assignee: Price Industries, Inc., Suwanee, GA (US)

( * ) Notice: Subject to any disclaimer, the term of this patent is extended or adjusted under 35 U.S.C. 154(b) by 393 days.

(21) Appl. No.: 17/898,666

(22) Filed: Aug. 30, 2022

(65) Prior Publication Data

US 2023/0144273 A1    May 11, 2023

Related U.S. Application Data

(60) Provisional application No. 63/238,528, filed on Aug. 30, 2021.

(51) Int. Cl.
*A61L 9/22* (2006.01)
*A61L 9/20* (2006.01)

(52) U.S. Cl.
CPC .................. *A61L 9/22* (2013.01); *A61L 9/20* (2013.01); *A61L 2209/12* (2013.01); *A61L 2209/14* (2013.01)

(58) Field of Classification Search
CPC .................... A61L 9/20; A61L 9/22
See application file for complete search history.

(56) References Cited

U.S. PATENT DOCUMENTS

| | | | | |
|---|---|---|---|---|
| 5,997,619 | A * | 12/1999 | Knuth | B01D 46/0038 55/385.2 |
| 2013/0291735 | A1* | 11/2013 | Livchak | F24F 1/0047 165/48.1 |
| 2014/0366734 | A1* | 12/2014 | Moro Franco | B60H 3/0078 96/60 |
| 2023/0270908 | A1* | 8/2023 | Lehmann | B01D 53/323 422/121 |

* cited by examiner

*Primary Examiner* — Kevin Joyner
(74) *Attorney, Agent, or Firm* — Artegis Law Group, LLP

(57) ABSTRACT

Disclosed herein is a room air purification unit. The room air purification unit can comprise a filtration apparatus, a blower, a purification chamber, and an outer housing. The filtration apparatus can be configured to cause a filtration of air from a setting in which the room air purification unit is located when the air flows through the filtration apparatus. The blower can be configured to cause the air from the setting to flow through the filtration apparatus and into an inlet of the blower and to expel the air from an outlet of the blower. The purification chamber can be configured to receive the air from the blower and to cause a purification the air when the air flows through the purification chamber. The outer housing can enclose the filtration apparatus, the blower, and the purification chamber.

13 Claims, 16 Drawing Sheets

ROOM AIR PURIFICATION UNIT

CROSS-REFERENCE TO RELATED APPLICATIONS

This application claims the benefit of and priority to U.S. Provisional Application No. 63/238,528, filed Aug. 30, 2021, and entitled "ROOM AIR PURIFICATION UNIT," which is incorporated by reference herein in its entirety.

BACKGROUND

In indoor settings like offices, circulated air can include dust, airborne pathogens, and other airborne particles that can have a negative effect on health. Thus, steps can be taken to ensure that the air is clean and safe. Unfortunately, filtration systems installed in indoor settings are often ineffectual because they operate at low efficiencies, if any filtration systems are installed at all. High-efficiency filtration is rarely present in indoor settings and adding high-efficiency filtration to those settings may not be feasible. In addition, filtration systems may only filter air without purifying and clearing that air.

BRIEF DESCRIPTION OF THE DRAWINGS

For a more complete understanding of the embodiments and the advantages thereof, reference is now made to the following description, in conjunction with the accompanying figures briefly described as follows.

Figure 1A:
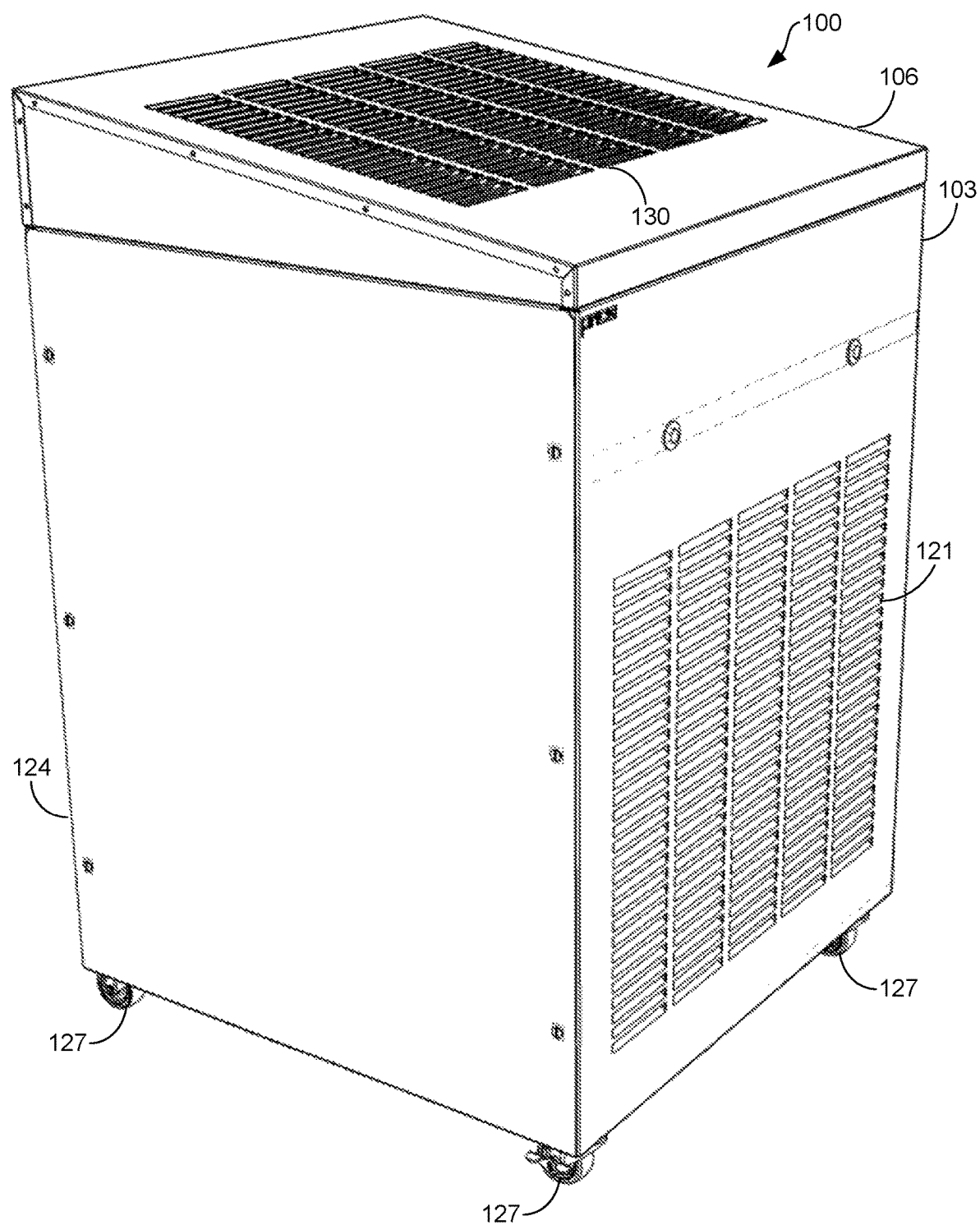
FIGS. 1A-C illustrate examples of perspective views of the room air purification unit, according to various embodiments of the present disclosure.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION

In the following paragraphs, the embodiments are described in further detail by way of example with reference to the attached drawings. In the description, well known components, methods, and/or processing techniques are omitted or briefly described so as not to obscure the embodiments. As used herein, the "present disclosure" refers to any one of the embodiments described herein and any equivalents. Furthermore, reference to various feature(s) of the "present embodiment" is not to suggest that all embodiments must include the referenced feature(s).

Disclosed herein is a room air purification unit that can efficiently filter and purify air in a room or other setting. The room air purification unit can filter air at a higher efficiency than filtration solutions in typical settings. For example, the room air purification unit can use a high efficiency particulate air (HEPA) filter to continually clean the air. As another example, the room air purification unit can a use lower-efficiency filter in addition to HEPA filter to filter larger particles from air before the air enters the HEPA filter, thereby increasing a usable life of the HPEA filter. The room air purification unit can substantially increase the quantity of air changes in a setting relative to typical settings. The room air purification unit can even surpass the standards set by The American Society of Heating, Refrigerating and Air-Conditioning Engineers (ASHRAE) for number of HEPA-filtered air changes per hour.

In addition, the room air purification can further treat the filtered air using, for example, ultraviolet radiation and bipolar ionization. Conventional systems, though, are often unable to incorporate filtration, ultraviolet radiation, and bipolar ionization in a single unit. This is due in part to the risks posed by ultraviolet radiation. For example, if a conventional filtration unit incorporated ultraviolet radiation, components in the conventional filtration unit could be damaged by the ultraviolet radiation. Examples of the disclosure can separate the ultraviolet radiation from other components of the room air purification unit to prevent these components from becoming damaged. Additionally, people who are near a conventional filtration unit could be harmed by ultraviolet radiation that escaped the unit at the point through which air flows from the unit. In contrast, the room air purification unit can separate the ultraviolet radiation from the point at which air flows out of the room air purification unit to prevent harm to any persons located proximate to this point. Thus, the room air purification unit can mitigate the risks posed by ultraviolet radiation while still allowing air to flow through the room air purification unit and be filtered and purified. The room air purification unit can likewise be constructed in a way that optimizes the filtration and treatment using ultraviolet radiation and bipolar ionization, which can allow substantially all of the air that flows through the room air purification unit to be exposed to the ultraviolet radiation and bipolar ionization after that air has been filtered.

The room air purification unit can be a standalone unit that does not need to be connected to a building's heating, ventilation, and air conditioning (HVAC) ductwork. Likewise, the room air purification unit can be self-contained in a package that can be easily incorporated into existing indoor settings. The room air purification unit can also be mobile, which can allow the room air purification unit to be located and re-located to rooms or areas where air purification is desired. This allows the flexibility to select settings in which to use the room air purification unit based on each setting's respective air quality requirements, as well as to move the room air purification unit to different settings if those air quality requirements change. The room air purification unit can provide access to internal components on multiple sides for maintenance and service. In some examples, maintenance can be performed on the room air purification unit without using tools.

Figure 1B:
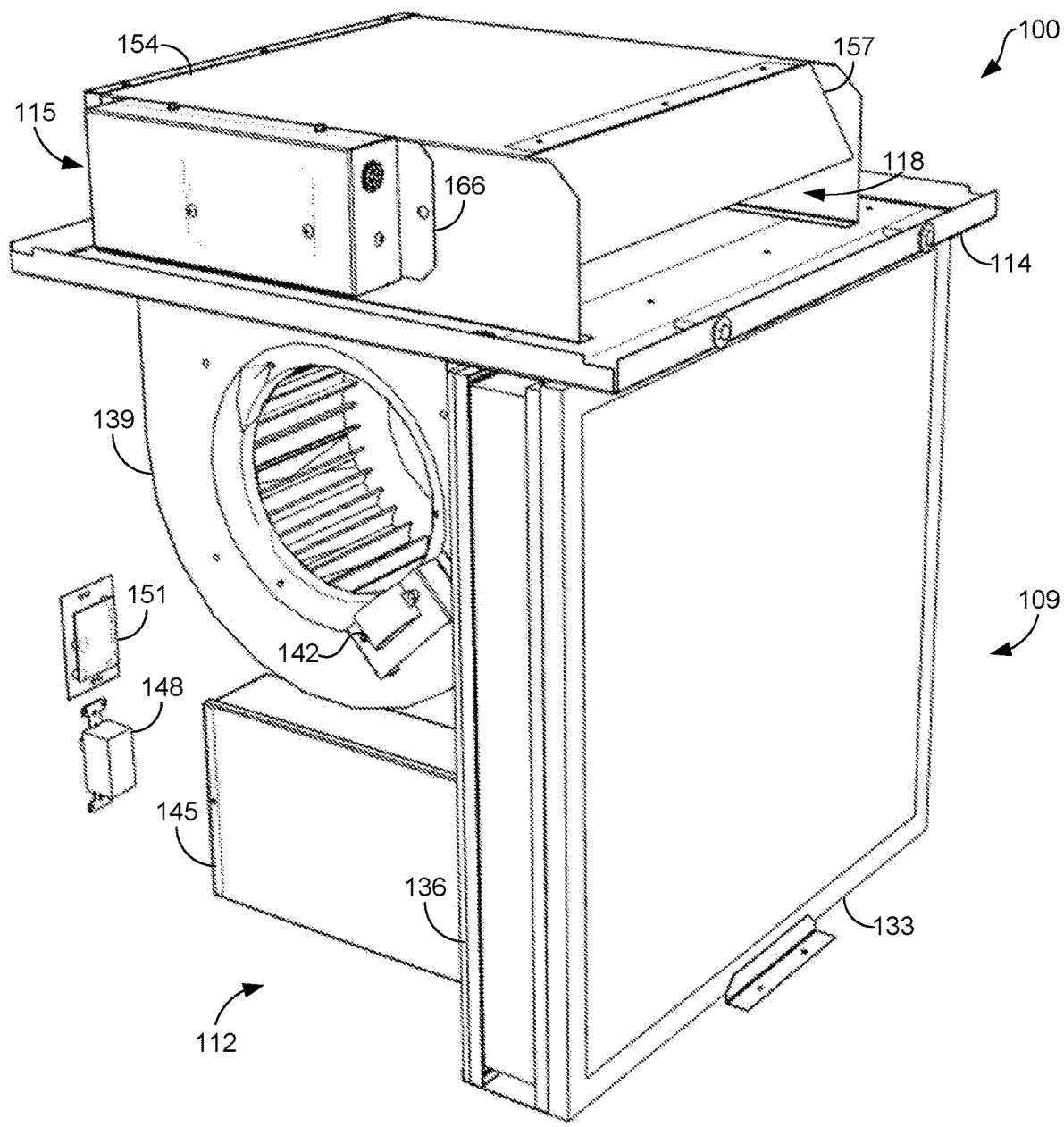
Figure 1C:
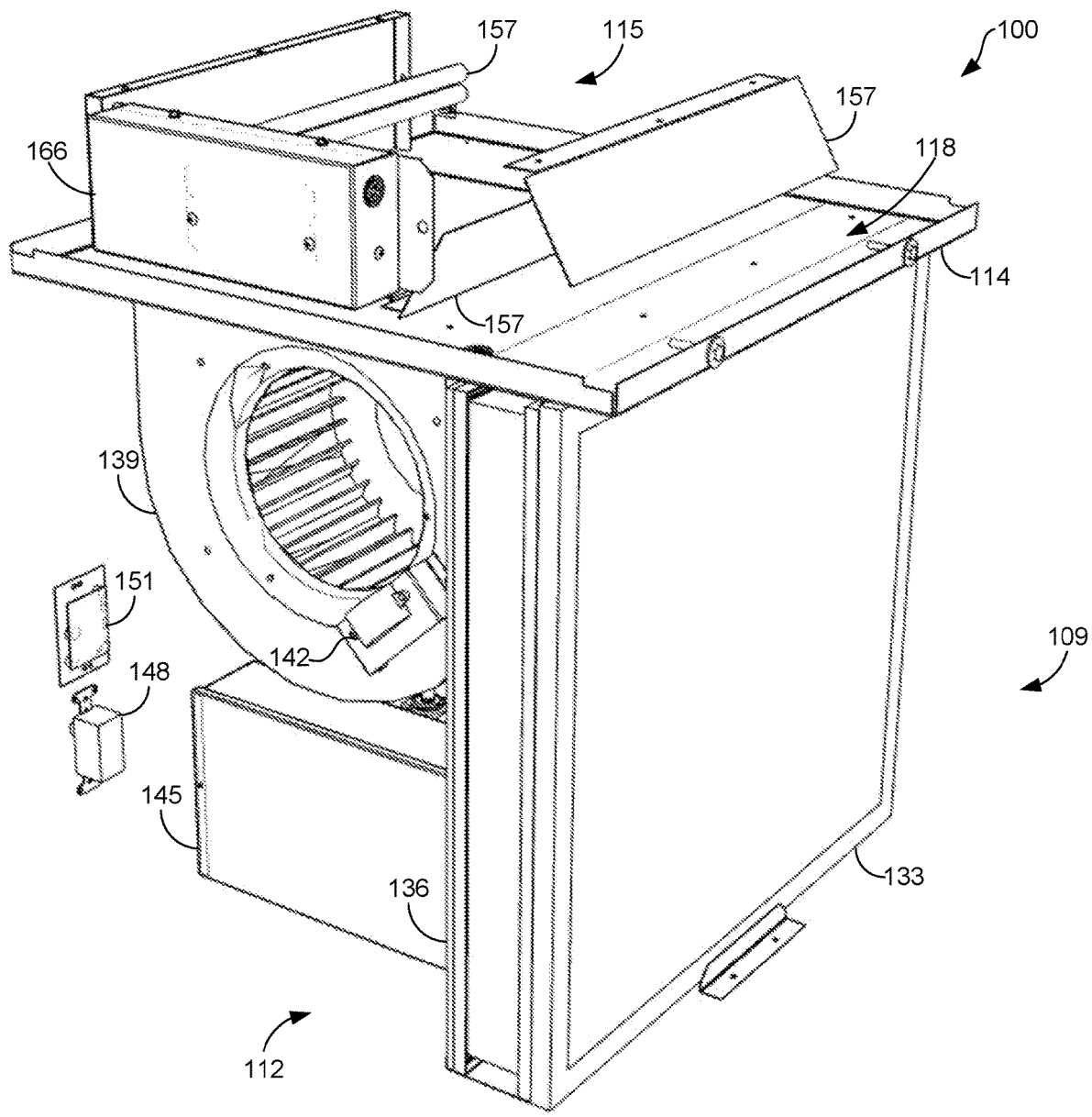

FIGS. 1A-C illustrate examples of perspective views of the room air purification unit 100. FIG. 1A shows an outside of the room air purification unit 100, while FIGS. 1B and 1C show internal components of the room air purification unit 100. The room air purification unit can include an outer housing 103, a top cover 106, a filtration apparatus 109, a lower chamber 112, a separator deck 114, a purification chamber 115, and an upper chamber 118.

The outer housing 103 can enclose internal components of the room air purification unit 100. In some examples, the outer housing 103 can be made from galvanized steel that can resist corrosion and damage. And in some examples, the outer housing 103 can be coated with a powder coat finish that can withstand corrosive cleaning agents.

The outer housing 103 can include an intake grille 121 and access panels 124. The intake grille 121 can be a grating, screen, register, or other group of openings through which air can enter the room air purification unit 100. The access panels 124 can be removed to provide access to internal components of the room air purification unit 100 for maintenance. Casters 127 can be attached to a bottom surface of the outer housing 103 to provide greater mobility of the room air purification unit 100. In some examples, the casters 127 can be lockable to allow the room air purification unit 100 to remain stationary and prevent accidental or unauthorized movement of the room air purification unit 100.

The top cover 106 can be a cover placed over an upper portion of the room air purification unit 100 on top of the outer housing 103. In some examples, the top cover 106 can be made from galvanized steel that can resist corrosion and damage. And in some examples, the top cover 106 can be coated with a powder coat finish that can withstand corrosive cleaning agents. In some examples, the top cover 106 can be removable to provide access to internal components of the room air purification unit 100 for maintenance.

The top cover 106 can include a discharge grille 130. The discharge grille 130 can be a grating, screen, register, or other group of openings through which air can exit the room air purification unit 100. Air can exit the room air purification unit 100 through the discharge grille 130 at an upward angle relative to an angle at which air enters the room air purification unit 100. That way, air that has been purified by the room air purification unit 100 does not immediately re-enter the room air purification unit 100 through the intake grille 121.

In some examples, the top cover 106 can be sloped relative to the outer housing 103 to deter storage of items on top of the room air purification unit 100. Items stored on top of the room air purification unit 100 could otherwise block the discharge grille 130. This can prevent the flow of air out of the room air purification unit 100 from being inhibited.

The filtration apparatus 109 can include one or more filters, combination of filters, or other filtration means by which air that enters the room air purification unit 100 can be filtered. The filtration apparatus 109 can include, for example, a pre-filter 133 and a filter 136. The pre-filter 133 and the filter 136 can be any devices designed to remove airborne particulate matter from air or other gasses that flow through them. The filtration apparatus 109 can be positioned proximate to the intake grille 121 so that air is filtered before entering the lower chamber 112. For example, the pre-filter 133 can be positioned between the intake grille 121 and the filter 136, and the filter 136 can be positioned between the pre-filter 133 and the lower chamber 112. The pre-filter 133 can be secured by brackets attached to a bottom surface of the outer housing 103 and to the separator deck 114. The filter 136 can be secured within a frame that is attached to a bottom surface of the outer housing 103 and to the separator deck 114. The pre-filter 133 can rest against an outer surface of this frame. The pre-filter 133 and the filter 136 can be accessed for removal and replacement by removing one of the access panels 124.

In some examples, the pre-filter 133 can be a lower-efficiency filter while the filter 136 can be a higher-efficiency filter. The pre-filter 133 can collect larger airborne particles so that only smaller airborne particles pass into the filter 136. This can reduce damage to the filter 136 caused by larger particles and allow the filter 136 to be changed less frequently. The pre-filter 133 can be, for example, a low- or medium-efficiency filter, an electrostatic filter, a washable filter, a fiberglass filter, a pleated filter, or any other suitable air filter. A pre-filter 133 can be chosen based on a Minimum Efficiency Reporting Value (MERV) rating sufficient to filter particles large enough to damage the filter 136. The filter 136 can be, for example, a high-efficiency particulate air (HEPA) filter, an electrostatic filter, a washable filter, a fiberglass filter, a pleated filter, or any other suitable air filter. A filter 136 can be chosen based on a MERV rating needed in the setting in which the room air purification unit 100 will be used. The pre-filter 133 and the filter 136 can also be shaped specially to fit within the room air purification unit 100.

The lower chamber 112 can be a chamber into which air flows after being filtered through the filtration apparatus 109 and before flowing into the purification chamber 115. The lower chamber 112 can be located in a lower portion of the room air purification unit 100 below the purification chamber 115 and the upper chamber 118. An upper boundary of the lower chamber 112 can be defined by a separator deck 114, and a lower boundary of the lower chamber 112 can be defined by a bottom surface of the outer housing 103. Lateral boundaries of the lower chamber 112 can be defined by the filtration apparatus 109 and lateral surfaces of the outer housing 103, including the access panels 124. The lower chamber 112 can include a blower 139, a bipolar ionization unit 142, a control module 145, a power switch 158, and an air flow controller 151.

The blower 139 can create pressure that pulls air through the filtration apparatus 109 and into the lower chamber 112. The blower 139 can be located in the lower chamber 112 proximate to the filtration apparatus 109 and the bipolar ionization unit 142. A motor can cause an impeller within the blower 139 to spin and pull air into one or more inlets on the sides of the blower 139. The impeller can then expel the air from an outlet at a top of the blower and into the purification chamber 115. The blower 139 can be accessed for maintenance by removing one of the access panels 124.

While in FIGS. 1B, 1C, 2C, 3B, 4B, 4C, and 5B the blower 139 is a centrifugal blower, the blower 139 can be any system designed to push and pull air. For example, the blower 139 can be a centrifugal blower, a high-speed blower, an axial fan, a backwards inclined fan, a plug fan, or any other suitable type of blower. The blower used can depend on the components used in the filtration apparatus 109. For example, if the filter 136 used in the filtration apparatus 109 is a HEPA filter, a blower 139 can be used that is designed to intake air at a velocity suitable for moving that air through the filter 136.

The bipolar ionization unit 142 can treat the air that has been filtered through the filtration apparatus 109. The bipolar ionization unit 142 can be any device designed to produce ions that can cluster around airborne pathogens and cause other airborne particles to clump together. As an example, the bipolar ionization unit 142 can do so by creating and emitting positive and negative oxygen ions without also creating ozone. In some examples, a bipolar ionization unit 142 can be used that requires little-to-no servicing or maintenance.

The bipolar ionization unit 142 can be located in the lower chamber 112 and secured to the blower 139 or other surface in the lower chamber 112. The bipolar ionization unit 142 can be secured using, for example, a mounting bracket. The bipolar ionization unit 142 can be located proximate to the blower 139 so that ions produced by the bipolar ionization unit 142 are immediately taken into the blower 139 at a high velocity. This can minimize collisions between ions and ensure a high concentration of ions in the air, as well as preventing ions from being caught in the filtration apparatus 109. In some examples, however, the bipolar ionization unit 142 may be omitted, or another component for treating the air may be used in its place.

The control module 145 can include various components used to control operation of the room air purification unit 100. The control module 145 can be secured to an inner surface of the outer housing 103 within the lower chamber 112. In some examples, however, the control module 145 may be located outside of the lower chamber 112 and secured to an outer surface of the outer housing 103.

The power switch 148 can be any electrical device designed to activate and deactivate the room air purification unit 100. The air flow controller 151 can be any device used to control a speed of airflow in and out of the room air purification unit 100 once the room air purification unit 100 has been activated using the power switch 148. The air flow controller 151 can control a speed at which the motor of the blower 139 operates. In some examples, the air flow controller 151 can allow for selection of one or more set speeds. In other examples, the air flow controller 151 can allow for selection of a variable speed. The air flow controller 151 can in some examples be controlled by a computing device such that the computing device can control the airflow speed of the room air purification unit 100. The air flow controller 151 can in some examples be automated to set an airflow speed of the room air purification unit 100 based on conditions like a size of the setting in which the room air purification unit 100 is located.

The power switch 148 and the air flow controller 151 can each be secured within the lower chamber 112 to an inner surface of the outer housing 103. The power switch 148 and the air flow controller 151 can be secured proximate to an aperture in the outer housing 103 to provide access to the power switch 148 and the air flow controller 151 from outside of the room air purification unit 100. In some examples, the power switch 148 and the air flow controller can be connected to the control module 145.

The separator deck 114 can separate the lower chamber 112 from the purification chamber 115 and the upper chamber 118. The blower 139 can expel air from the lower chamber 112 and into the purification chamber 115 through an aperture in the separator deck 114. The separator deck 114 can be secured to lateral surfaces of the outer housing 103.

The purification chamber 115 can be a chamber in which air that has been filtered can be purified. The purification chamber 115 can include a purification chamber housing 154, baffles 157, an ultraviolet lamp 160, and an ultraviolet module 163. The purification chamber 115 can be located in an upper portion of the room air purification unit 100 above the lower chamber 112. Boundaries of the purification chamber 115 can be defined by the separator deck 114 the purification chamber housing 154, and one or more of the baffles 166.

The purification chamber housing 154 can enclose the ultraviolet lamp 160 and contain air within a space sufficient to allow substantially all of the air to be treated by the ultraviolet lamp 160. The purification chamber housing 154 can be positioned over the aperture in the separator deck 114 so that air expelled from the blower is contained within the purification chamber 115 and treated by the ultraviolet lamp 160 before the air leaves the purification chamber 115. This design also prevents items dropped into the room air purification unit 100 through the discharge grille 130 from falling into the blower 139 and causing damage. In some examples, the purification chamber housing 154 can be made from, for instance, galvanized steel.

The baffles 157 can be any panels or other devices that can obstruct and direct the flow of the air. The baffles 157 can be connected to or located proximate to the purification chamber housing 154 and angled in a way that directs air out of the purification chamber 115 while containing the air withing the purification chamber 115 for sufficient time to allow the air to be treated by the ultraviolet lamp 160. In some examples, the baffles 157 can be made from, for instance, galvanized steel.

In some examples, inner surfaces of the purification chamber housing 154 and the baffles 157 can be reflective. This reflectivity can increase the intensity of ultraviolet radiation within the purification chamber 115. The increased intensity of the ultraviolet radiation can allow the air to be sufficiently treated by the ultraviolet lamp 160 during the time that the air is within the purification chamber 115. The purification chamber housing 154 and the baffles 157 can be made from a reflective material, or a reflective material can be applied to the inner surfaces of the purification chamber housing 154 and the baffles 157.

The purification chamber housing 154, the baffles 157, and the separator deck 114 can together prevent ultraviolet radiation from escaping the purification chamber 115. This can prevent the ultraviolet radiation from harming any persons present in the setting in which the room air purification unit 100 is located. This can also prevent the ultraviolet radiation from harming other components of the room air purification unit 100 like, for example, the pre-filter 133, the filter 136, or bipolar ionization unit 142. The purification chamber housing 154 can prevent ultraviolet radiation from escaping the purification chamber 115 into a setting in which the room air purification unit 100 is located. The baffles 157 can be angled to allow air to flow out of the purification chamber 115 while also preventing ultraviolet radiation from escaping the purification chamber 115 into the setting. The separator deck 114 can prevent ultraviolet radiation from escaping into the lower chamber 112.

The ultraviolet lamp 160 can treat the air that has been filtered through the filtration apparatus 109 and expelled by the blower 139 into the purification chamber 115. The ultraviolet lamp 160 can be any device designed to emit ultraviolet radiation capable of inactivating airborne pathogens. For example, the ultraviolet lamp 160 can be a UV-C lamp. The ultraviolet lamp 160 can be secured to an inner surface of the purification chamber housing 154 or to the separator deck 114. The ultraviolet lamp 160 can be accessed for removal and replacement by removing either of the access panels 124. In some examples, however, the ultraviolet lamp 160 may be omitted, or another purification component may be used in its place.

The ultraviolet module 163 can facilitate operation of the ultraviolet lamp 160. For example, the ultraviolet module 163 can include one or more components that allow the ultraviolet lamp 160 to function. The ultraviolet module 163 can be secured to an outer surface of the purification chamber housing 154 proximate to the ultraviolet lamp 160.

The upper chamber 118 can be a chamber into which air flows from the purification chamber 115 after being purified. The upper chamber 118 can be located in an upper portion of the room air purification unit 100 above the lower chamber 112. An upper boundary of the upper chamber 118 can be defined by the top cover 106, and a lower boundary of the upper chamber 118 can be defined by the separator deck 114 and the purification chamber housing 154. Lateral boundaries of the upper chamber 118 can be defined by lateral surface of the outer housing 103, including the access panels 124. Air can pass through the upper chamber 118 and be expelled from the upper chamber 118 through the discharge grille 130.

As discussed above, the access panels 124 can be removed to provide access to internal components of the room air purification unit 100 for maintenance. For example, either of the access panels 124 can be removed to provide access to the pre-filter 133 and filter 136 so that the pre-filter 133 or the filter 136 can be removed and replaced. As another example, either of the access panels 124 can be removed to provide access to components of the lower chamber 112 like the blower 139, bipolar ionization unit 142, control module 145, power switch 148, or air flow controller 151. The blower 139, bipolar ionization unit 142, control module 145, power switch 148, or air flow controller 151 can then be individually removed for maintenance or replaced altogether. As an additional example, the access panels 124 can be removed to provide access to components of the ultraviolet chamber like the ultraviolet lamp 160 and the ultraviolet module 163 for maintenance or replacement.

Figure 2A:
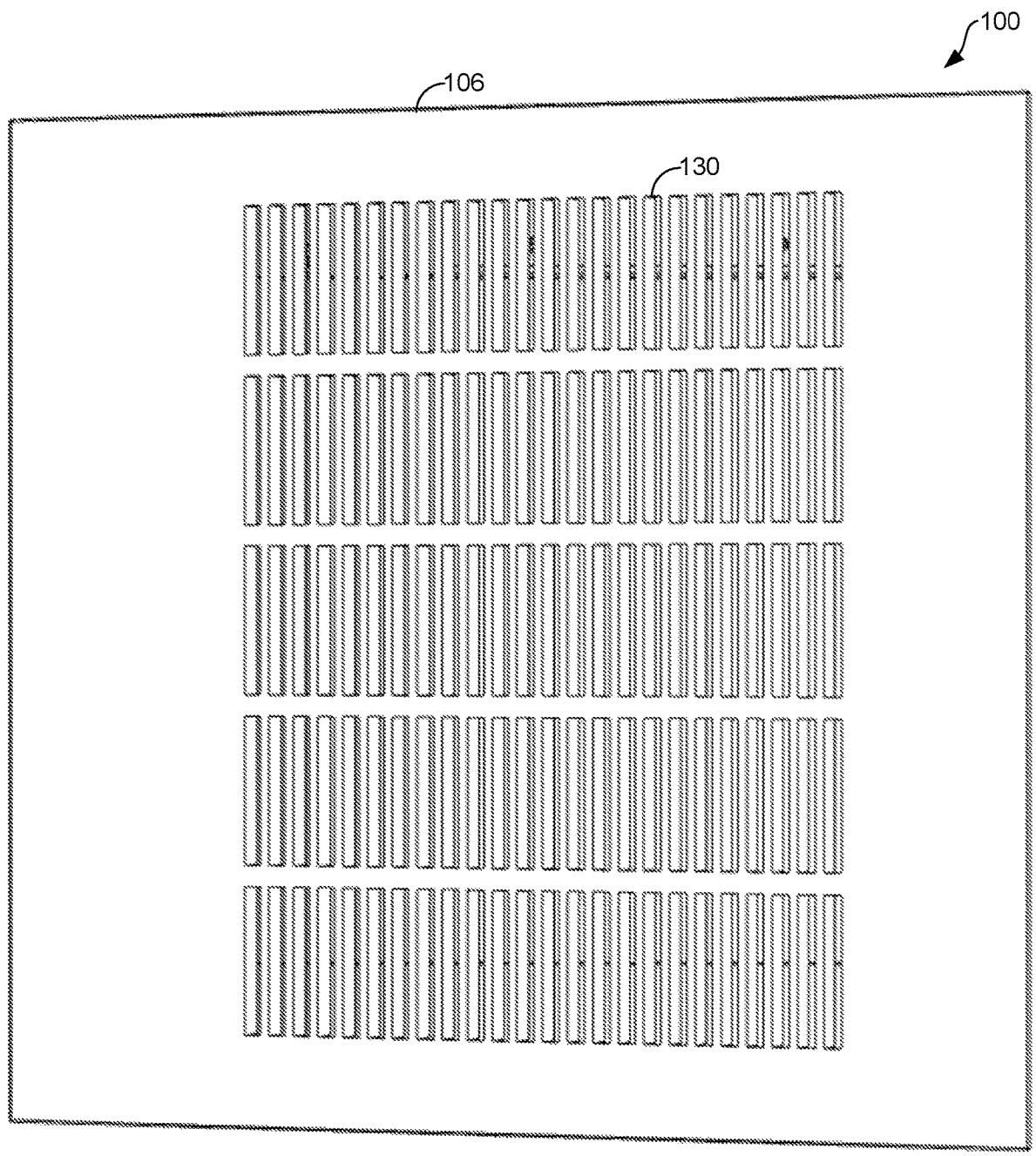
FIGS. 2A-C illustrate examples of top views of the room air purification unit, according to various embodiments of the present disclosure.
Figure 2B:
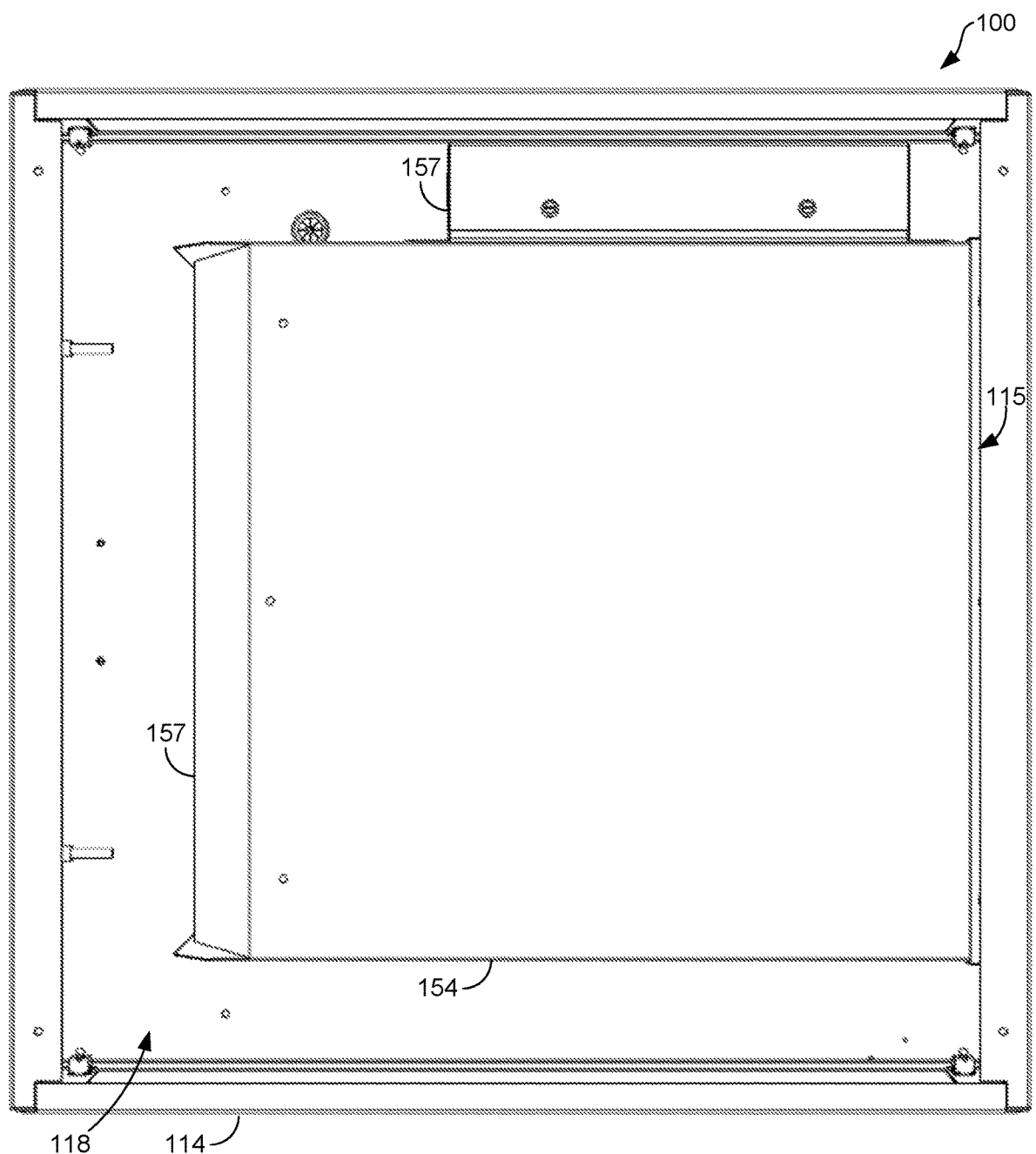
Figure 2C:
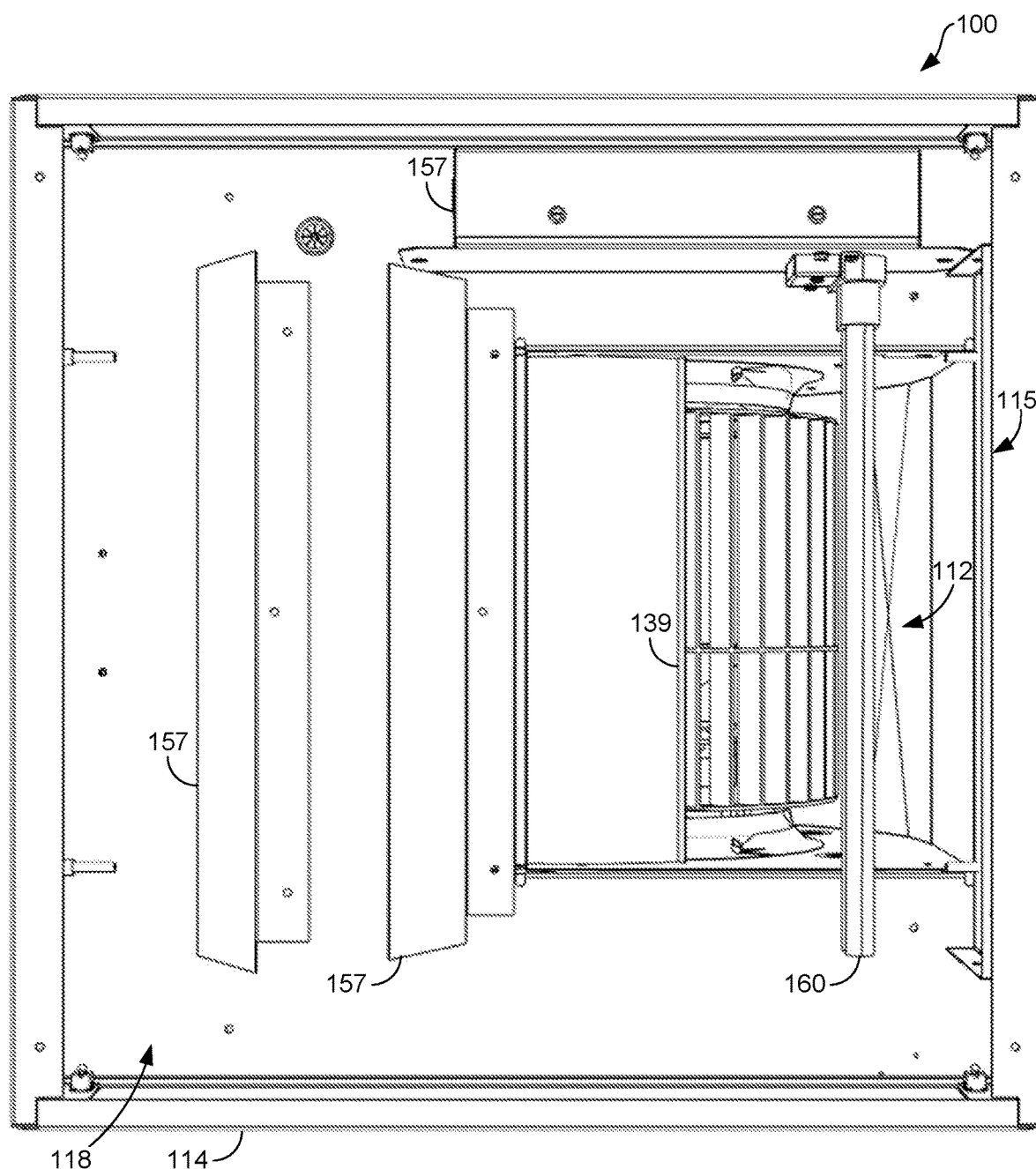

FIGS. 2A-2C illustrate examples of top views of the room air purification unit 100. FIG. 2A illustrates an outside of the room air purification unit 100 from a top view. FIG. 2A shows the top cover 106 and the discharge grille 130. FIGS. 2B and 2C illustrate internal components of the room air purification unit 100 from top views. FIG. 2B shows the internal components with the purification chamber housing 154 present, and FIG. 2C shows the internal components with at least a portion of the purification chamber housing 154 removed. FIG. 2B shows the separator deck 114, the purification chamber 115, the upper chamber 118, the purification chamber housing 154, the ultraviolet module 163, and a baffle 157. FIG. 2C shows the lower chamber 112, the separator deck 114, the purification chamber 115, the upper chamber 118, the blower 139, baffles 157, the ultraviolet lamp 160, and the ultraviolet module 163.

Figure 3A:
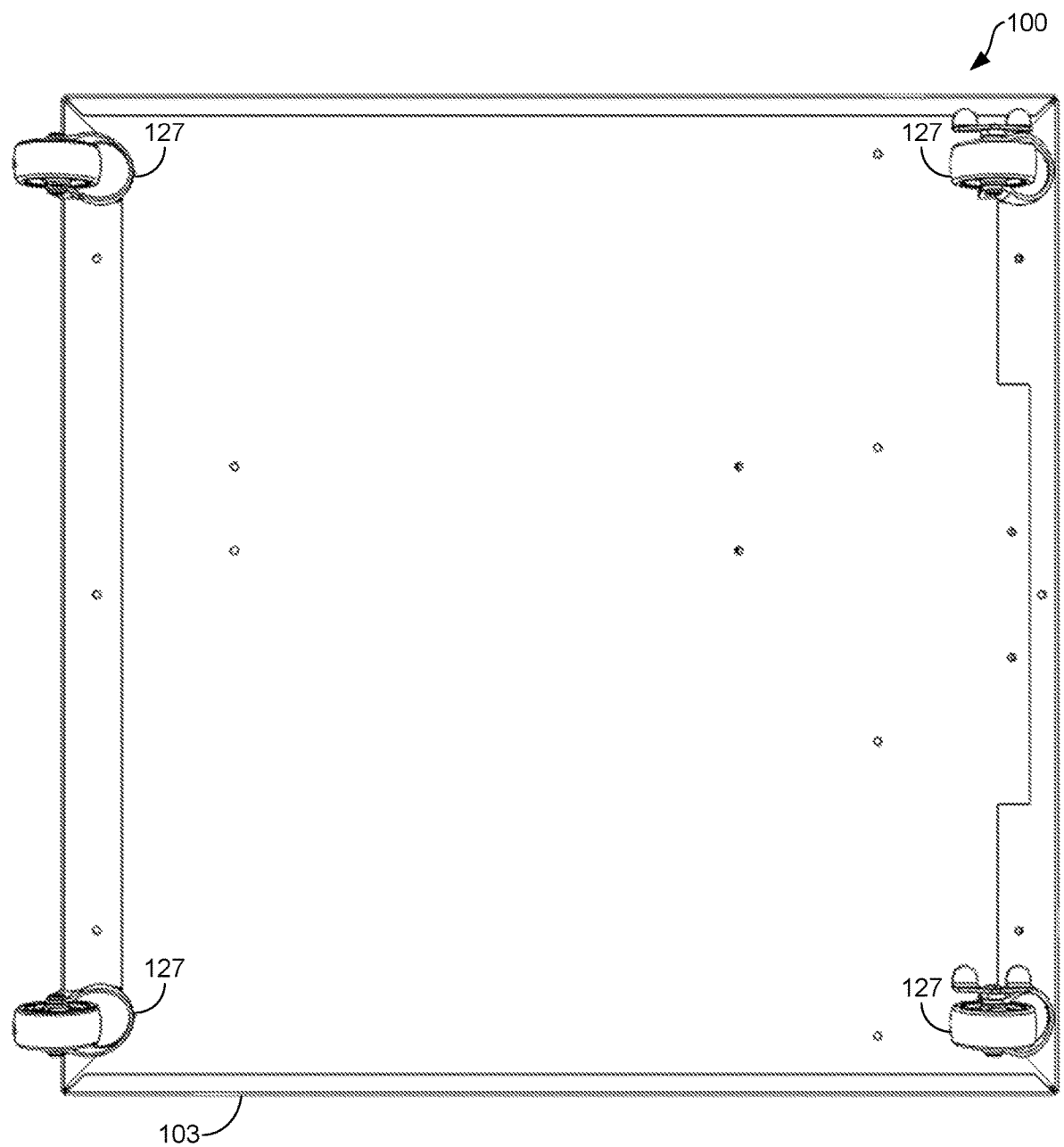
FIGS. 3A-B illustrate examples of bottom views of the room air purification unit, according to various embodiments of the present disclosure.
Figure 3B:
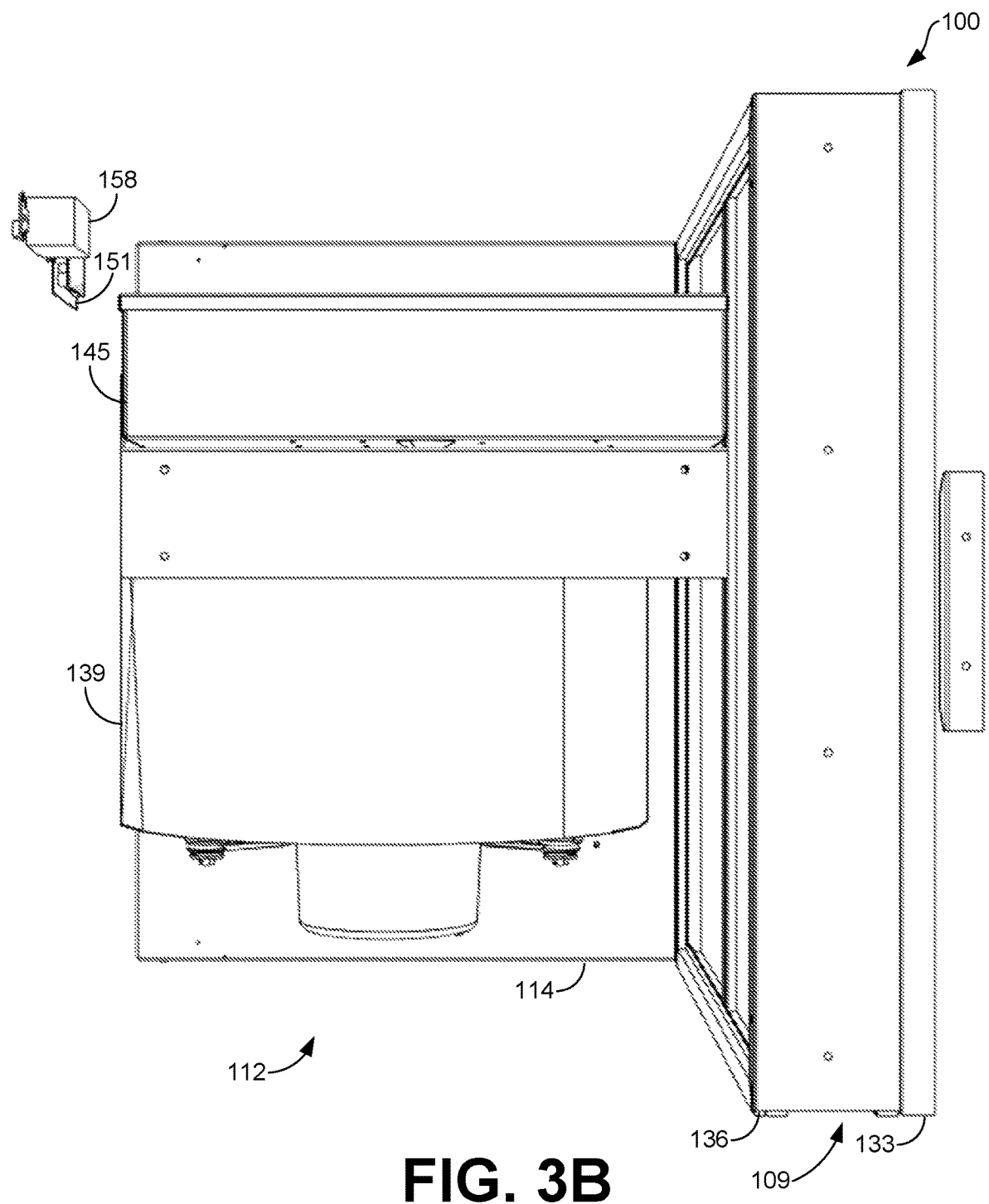

FIGS. 3A-B illustrate examples of bottom views of the room air purification unit 100. FIG. 3A illustrates an outside of the room air purification unit 100 from a bottom view. FIG. 3A shows the outer housing 103 and casters 127. FIG. 3B illustrates internal components of the room air purification unit 100 from a bottom view. FIG. 3B shows the filtration apparatus 109, the lower chamber 112, the pre-filter 133, the filter 136, the blower 139, the control module 145, the power switch 148, and the air flow controller 151.

Figure 4A:
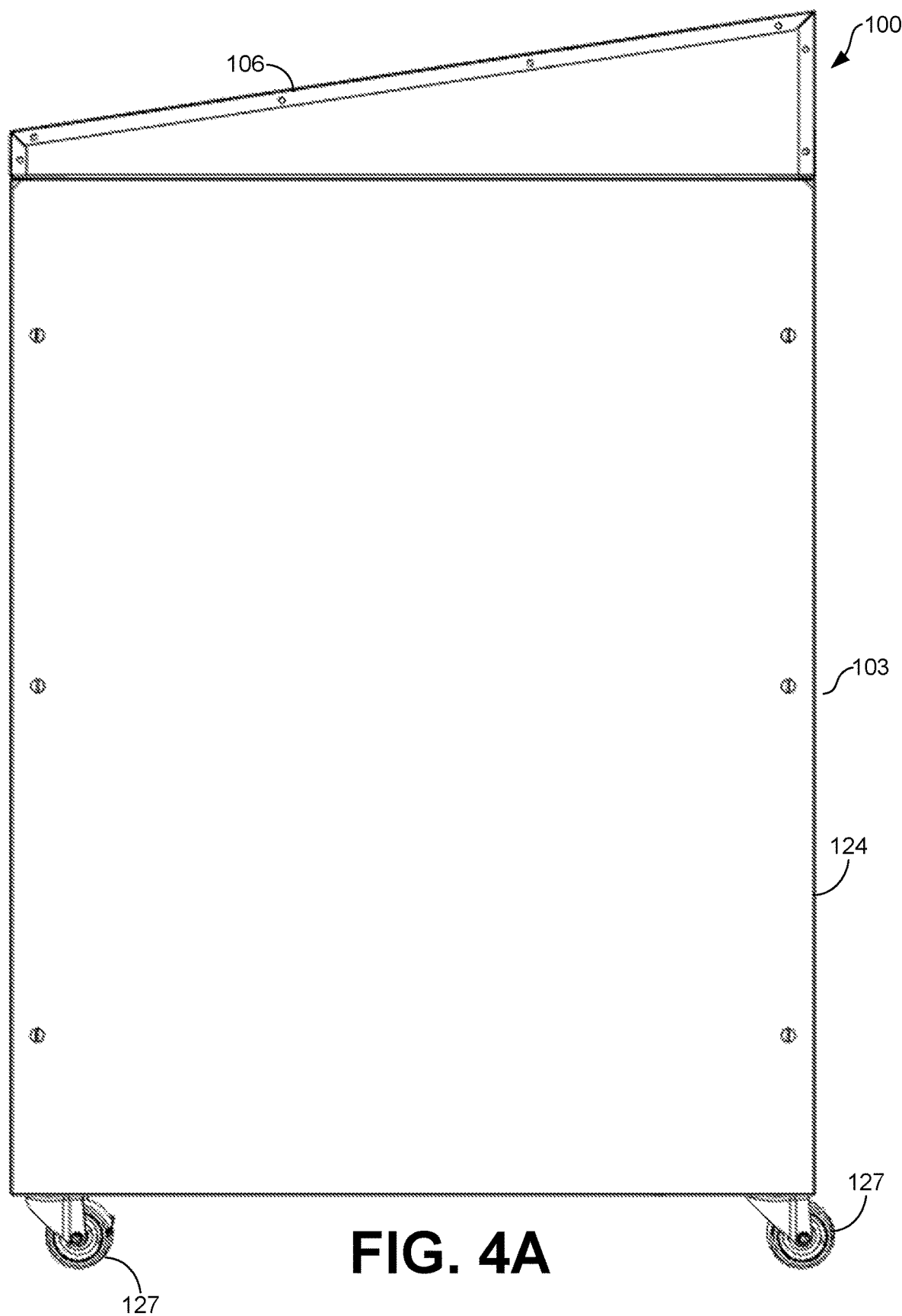
FIGS. 4A-C illustrate examples of first side views of the room air purification unit, according to various embodiments of the present disclosure.
Figure 4B:
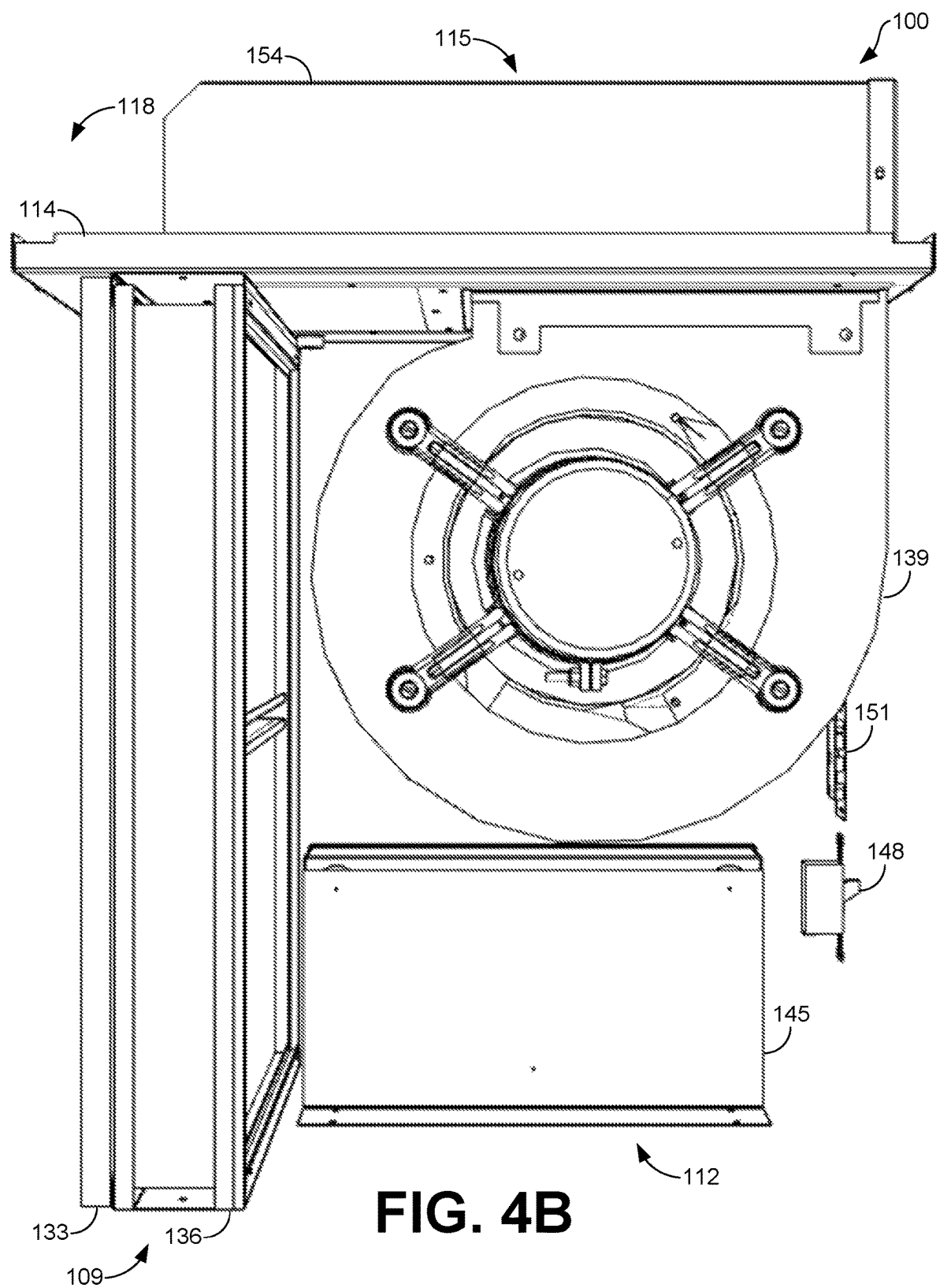
Figure 4C:
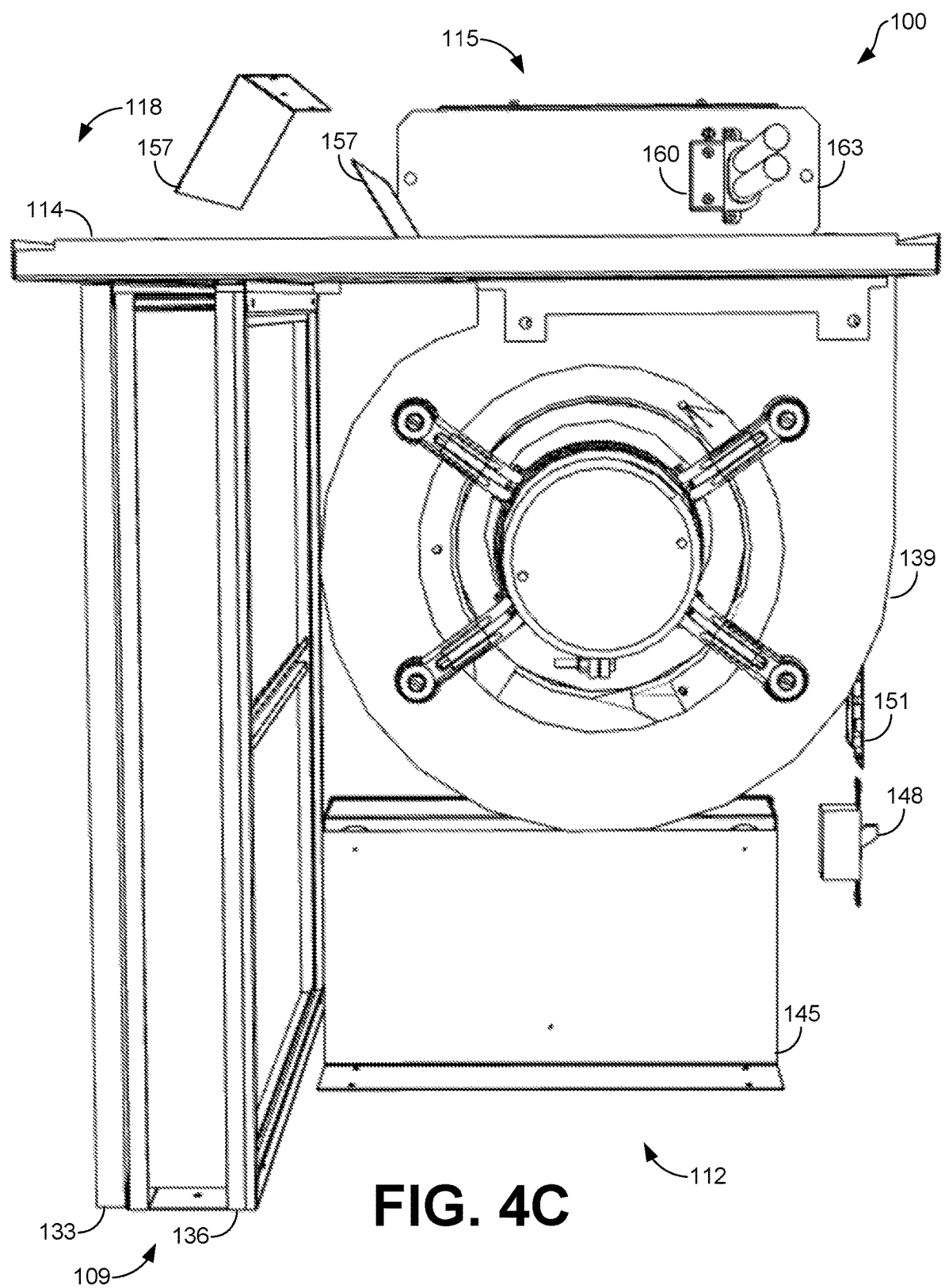

FIGS. 4A-C illustrate examples of first side views of the room air purification unit 100. FIG. 4A illustrates an outside of the room air purification unit 100 from a first side view, FIG. 4A shows the outer housing 103, the top cover 106, an access panel 124, and casters 127. FIGS. 4B and 4C illustrate internal components of the room air purification unit 100 from first side views. FIG. 4B shows the internal component with the purification chamber housing 154 present, and FIG. 4C shows the internal components with at least a portion of the purification chamber housing 154 removed. FIG. 4B shows the filtration apparatus 109, the lower chamber 112, the separator deck 114, the purification chamber 115, the upper chamber 118, the pre-filter 133, the filter 136, the blower 139, the control module 145, the power switch 148, the air flow controller 151, and the purification chamber housing 154. FIG. 4C shows the filtration apparatus 109, the lower chamber 112, the separator deck 114, the purification chamber 115, the upper chamber 118, the pre-filter 133, the filter 136, the blower 139, the control module 145, the power switch 148, the air flow controller 151, baffles 157, the ultraviolet lamp 160, and the ultraviolet module 163.

Figure 5A:
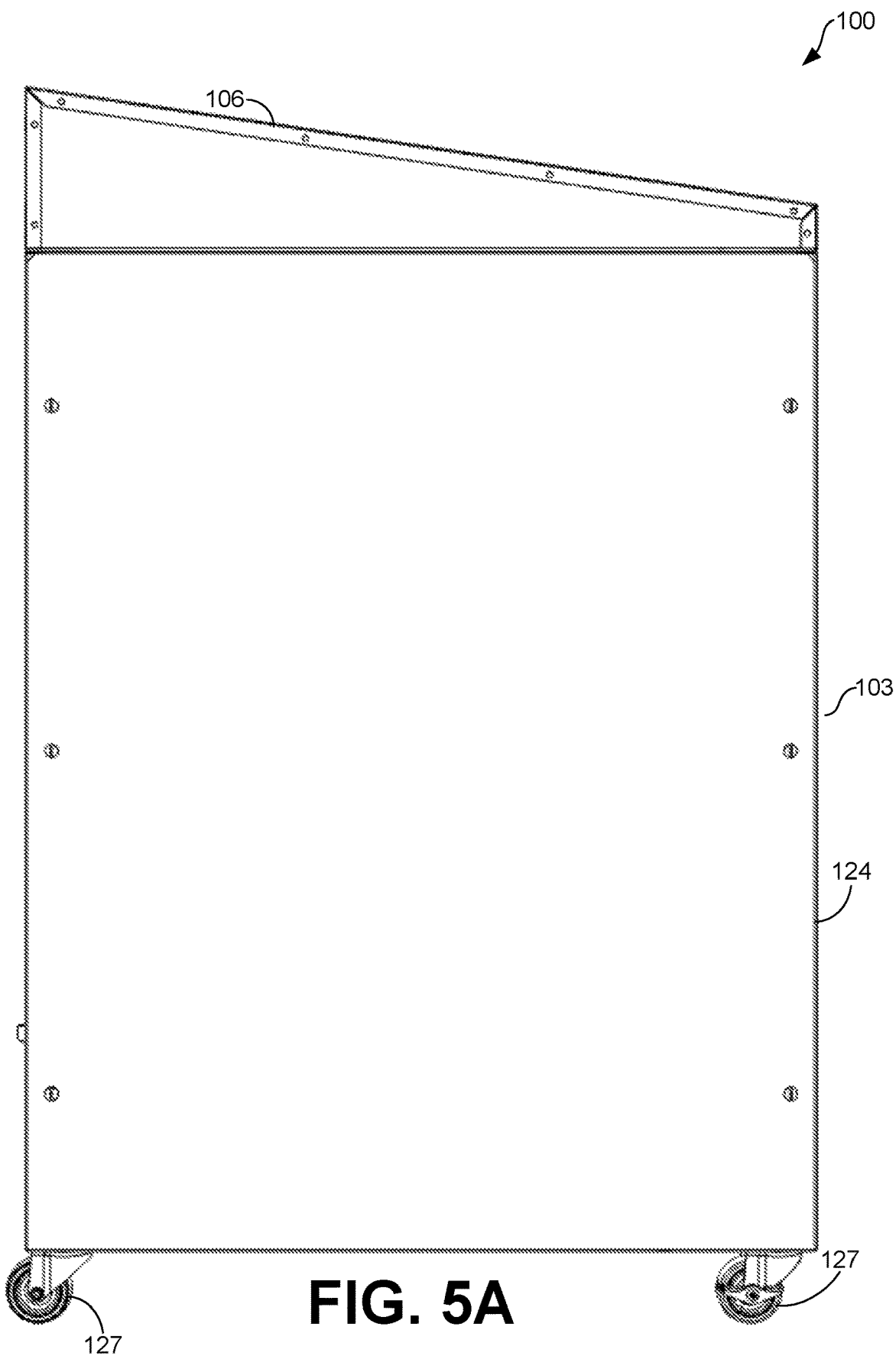
FIGS. 5A-B illustrate examples of second side views of the room air purification unit, according to various embodiments of the present disclosure.
Figure 5B:
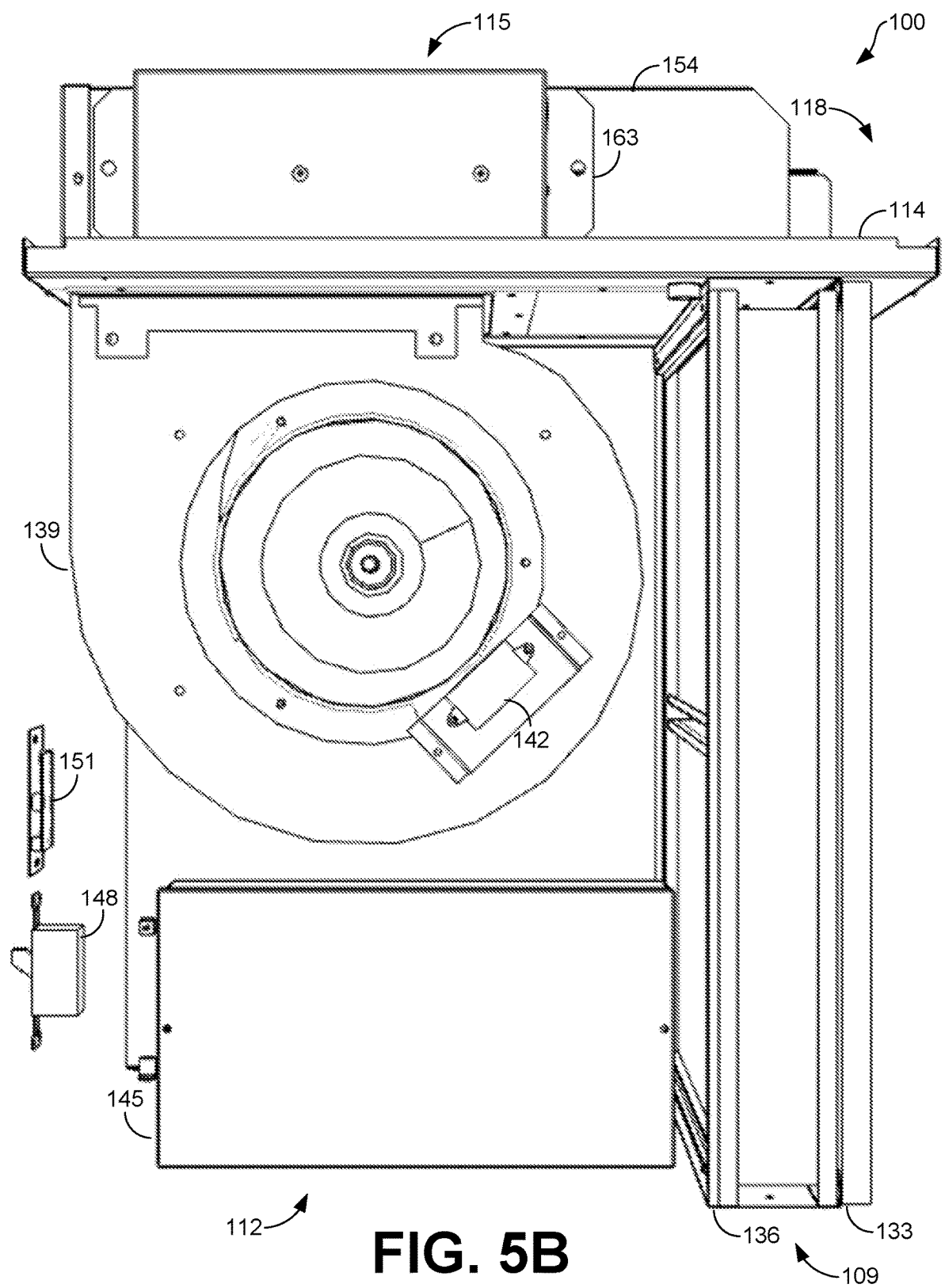

FIGS. 5A-B illustrate examples of second side views of the room air purification unit 100. FIG. 5A illustrates an outside of the room air purification unit 100 from a second side view. FIG. 5A shows the outer housing 103, an access panel 124, casters 127, and the top cover 106. FIG. 5B illustrates internal components of the room air purification unit 100 from a second side view. FIG. 5B shows the filtration apparatus 109, the lower chamber 112, the purification chamber 115, the separator deck 114, the upper chamber 118, the pre-filter 133, the filter 136, the blower 139, the bipolar ionization unit 142, the control module 145, the power switch 148, the air flow controller 151, the ultraviolet lamp 160, and the ultraviolet module 163.

Figure 6:
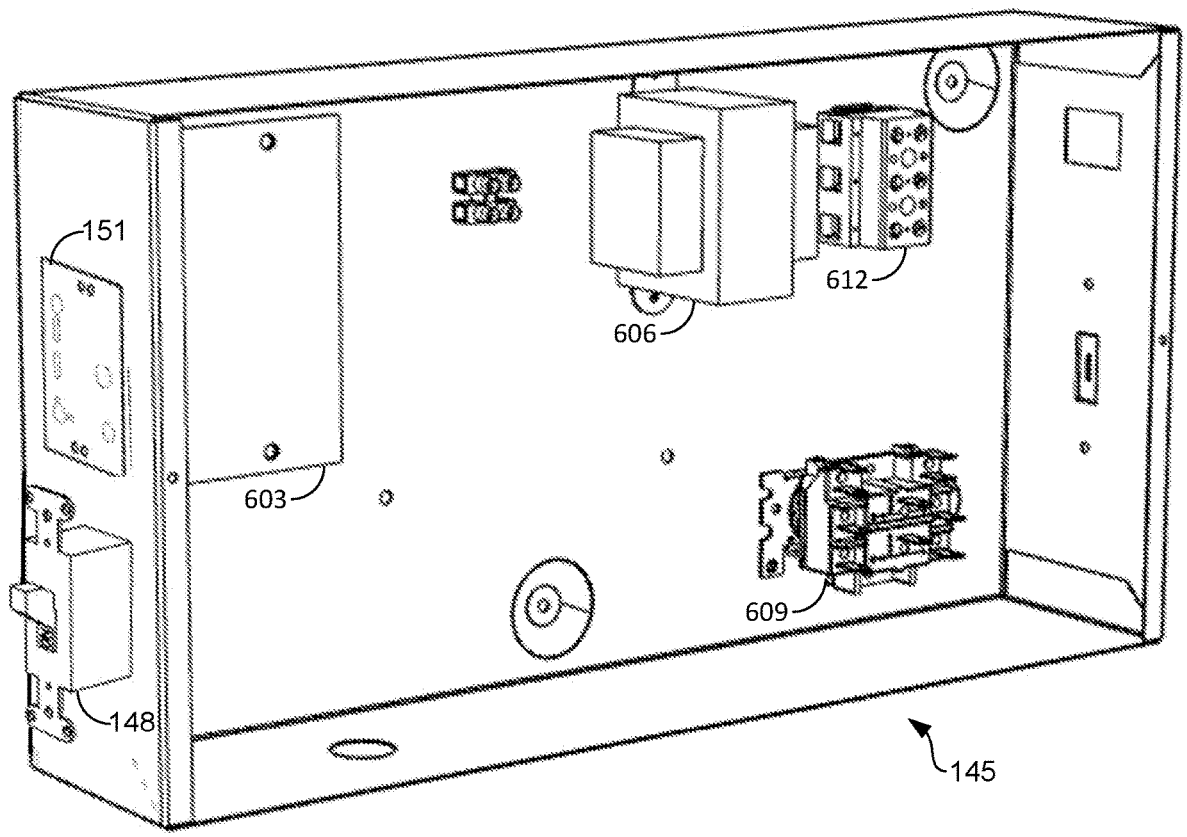
FIG. 6 illustrates an example of an isolated perspective view of a control module of the room air purification unit, according to various embodiments of the present disclosure.

FIG. 6 illustrates an example of an isolated perspective view of a control module 145 of the room air purification unit 100. In the example of FIG. 6, the power switch 158 and the air flow controller 151 are connected to the control module 145. In some examples, however, the power switch 158 and the air flow controller may be separate from the control module 145.

In the example of FIG. 6, the control module 145 includes a control unit 603, a transformer 606, a terminal block 609, and a fan relay 612, but the control module 145 can include different components in other examples. The control unit 603, transformer 606, terminal block 609, and fan relay 612 can be secured to an inside surface of the control module 145. The control unit 603 can be any microcontroller, circuit board, or other electronic device configured control operation of the various functions of the room air purification unit 100. The transformer 606 can be any electrical device designed to supply voltage used to operate the motor of the blower 139. The terminal block 609 can be any device designed to secure wires or any other connections used to operate the motor of the blower 139. The fan relay 612 can be any electrical device designed to relay power used to operate the motor of the blower 139.

Figure 7:
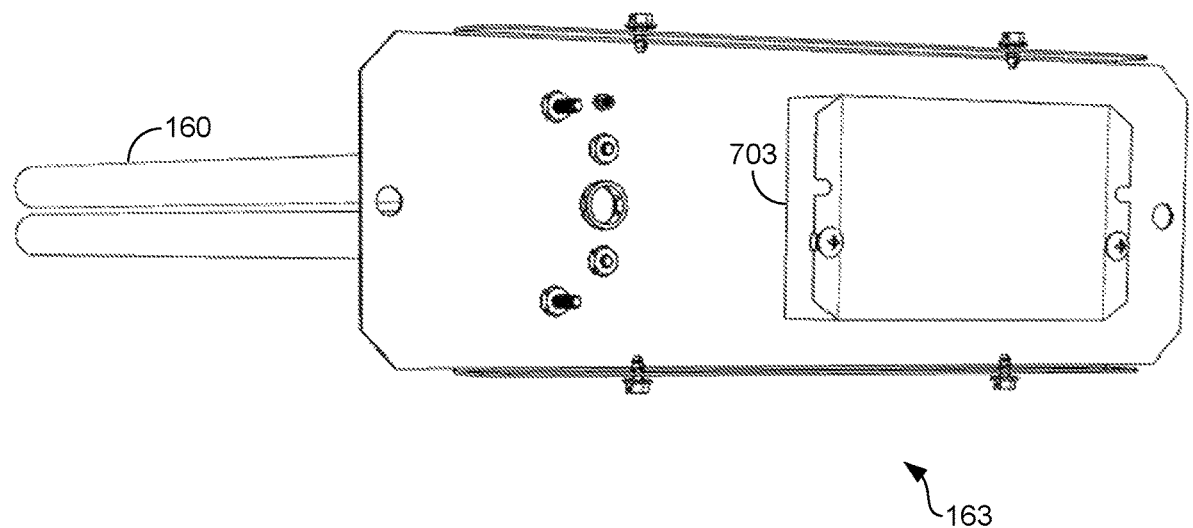
FIG. 7 illustrates an example of an isolated perspective view of an ultraviolet module of the room air purification unit, according to various embodiments of the present disclosure.

FIG. 7 illustrates an example of an isolated perspective view of an ultraviolet module 163 of the room air purification unit 100. The ultraviolet module 163 can include an ultraviolet ballast 703. The ultraviolet ballast 703 can be any electronic, magnetic, or electro-mechanical device designed to provide voltage sufficient to initiate the emission of ultraviolet radiation from the ultraviolet lamp 160 and to sustain the emission of the ultraviolet radiation during operation of the ultraviolet lamp 160.

Figure 8:
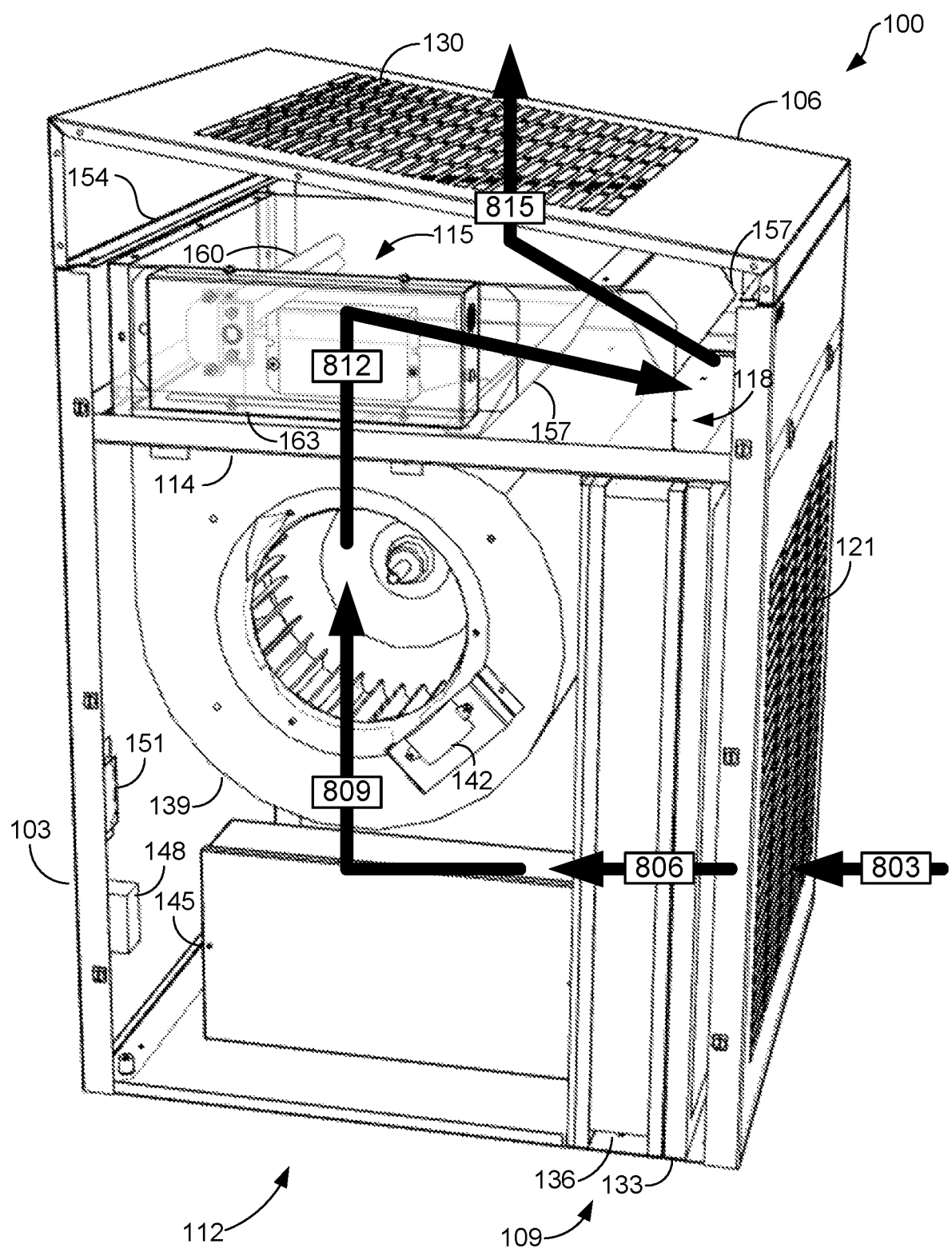
FIG. 8 illustrates an example of a flow diagram of a process for filtering and purifying air using the room air purification unit, according to various embodiments of the present disclosure.

FIG. 8 illustrates an example of a flow diagram of a process for purifying air using the room air purification unit. For purposes of illustration, a perspective view of the room air purification unit 100 is shown, with an access panel 124 and casters 127 not shown and the purification chamber housing 154 and ultraviolet module 163 shown as transparent.

At step 803, air can enter the room air purification unit 100 through the intake grille 121. The room air purification unit 100 can be activated using the power switch 148 and the speed of the air intake can be controlled using the air flow controller 151. When the room air purification unit 100 is activated, air can be pulled into the room air purification unit 100 by the blower 139. The air can enter from a room or other setting in which the room air purification unit 100 is located.

At step 806, the air can pass through the filtration apparatus 109. The air can first pass through the pre-filter 133, which can filter out larger airborne particles. The air can then pass through the filter 136, which can filter out smaller airborne particles. The air can be pulled through the pre-filter 133 and the filter 136 by the blower 139.

At step 809, the air can enter the lower chamber 112 after passing through the filtration apparatus 109. The air that enters the lower chamber 112 can be pulled into the blower 139 through an inlet on a side of the blower 139. The bipolar ionization unit 142 can produce ions that can be pulled into the blower 139 with the air and thereby mix with the air. These ions can cluster around airborne pathogens and cause other airborne particles to clump together. And because the air has already been filtered and because the ions are pulled quickly into the blower 139, these ions do not become caught in the filtration apparatus 109, ensuring an optimal concentration of ions in the air.

At step 812, the air can enter the purification chamber 115 through an aperture in the separator deck 114 after being expelled from the blower 139. While in the purification chamber 115, the air can be exposed to ultraviolet radiation produced by the ultraviolet lamp 160, which is powered using the ultraviolet module 163. The ultraviolet radiation can inactivate airborne pathogens in the air. The intensity of the ultraviolet radiation can also be increased by reflectivity of inner surfaces of the purification chamber housing 154 and the baffles 157. Because the purification chamber 115 is enclosed by the separator deck 114, the purification chamber housing 154, and the baffles 157, this ultraviolet radiation does not escape the purification chamber, preventing harm to other components of the room air purification unit and to any persons present outside of the room air purification unit. The air can then flow around the baffles 157 and out of the purification chamber 115.

At step 815, the air can enter the upper chamber 118. By this step, the air has been treated using ions produced by the bipolar ionization unit 142 and ultraviolet radiation produced by the ultraviolet lamp. Thus, the presence of airborne pathogens and other airborne particles in the air can be significantly reduced or eliminated compared to step 803 when the air entered the room air purification unit 100. The air can then flow out of the upper chamber 118 through the discharge grille 130, out of the room air purification unit 100, and into the room or other setting in which the room air purification unit 100 is located.

Therefore, at least the following is claimed:

1. A room air purification unit comprising:
a filtration apparatus within a lower chamber, the filtration apparatus configured to cause a filtration of air from a setting in which the room air purification unit is located when the air flows through the filtration apparatus;
a blower within the lower chamber, the blower configured to cause the air from the setting to flow through the filtration apparatus and into an inlet of the blower and to expel the air from an outlet of the blower, wherein the filtration apparatus is located between the blower and an intake grille;
a bipolar ionization unit within the lower chamber, the bipolar ionization unit configured to produce ions that mix with the air;
a purification chamber within a purification chamber housing, the purification chamber located above the blower, comprising at least one ultraviolet lamp, and being configured to receive the air from the blower to cause a purification the air when the air flows through the purification chamber, wherein the purification chamber further comprises a plurality of baffles oriented to contain ultraviolet radiation within the purification chamber, wherein the plurality of baffles comprise an exit baffle angled to allow the air to exit the purification chamber into an upper chamber while preventing ultraviolet radiation from escaping the purification chamber into the lower chamber;
a separator deck that separates the purification chamber housing from the lower chamber, wherein the separator deck together with the purification chamber housing prevents the ultraviolet radiation from entering the lower chamber;
an upper chamber located above the purification chamber receiving air from the purification chamber, wherein the purification chamber housing and the plurality of baffles prevent the ultraviolet radiation from entering the upper chamber and wherein the air from the purification chamber exits through a discharge grille adjacent to the upper chamber; and
an outer housing comprising the discharge grille and enclosing the filtration apparatus, the upper chamber, the blower, and the purification chamber, wherein the discharge grille is angled away from the intake grille and sloped relative to a bottom side of the outer housing.

2. The room air purification unit of claim 1, further comprising a control module configured to control an operation of the blower.

3. The room air purification unit of claim 1, wherein the filtration apparatus comprises a first filter and a second filter.

4. The room air purification unit of claim 3, wherein the first filter is positioned adjacent to an entry of the air to the room air purification unit, and the second filter is positioned between the first filter and the purification chamber.

5. The room air purification unit of claim 3, wherein the second filter has a higher efficiency than the first filter.

6. The room air purification unit of claim 1, wherein the purification chamber housing and the plurality of baffles comprise a reflective inner surface, the reflective inner surface causing an increase in an intensity of the ultraviolet radiation within the purification chamber.

7. An apparatus, comprising:
a filtration apparatus within a lower chamber, the filtration apparatus configured to cause a filtration of air from an external setting when the air passes through the filtration apparatus;
a purification chamber within a purification chamber housing, the purification chamber located above the lower chamber and being configured to receive the air from the lower chamber to cause a purification the air when the air flows through the purification chamber, wherein the purification chamber further comprises a plurality of baffles oriented to contain ultraviolet radiation within the purification chamber, wherein the plurality of baffles comprise an exit baffle angled to allow the air to exit the purification chamber into an upper chamber while preventing ultraviolet radiation from escaping the purification chamber into the lower chamber;

an ultraviolet lamp within the purification chamber, the ultraviolet lamp configured to generate the ultraviolet radiation and cause a treatment of the air when the air passes within a proximity of the ultraviolet lamp;

a blower within the lower chamber configured to cause the air to pass through the filtration apparatus and into an inlet of the blower, the blower causing the air to be expelled from an outlet of the blower, through the purification chamber and into upper chamber positioned above the purification chamber;

a separator deck that separates the purification chamber housing from the lower chamber, wherein the separator deck together with the purification chamber housing prevents the ultraviolet radiation from entering the lower chamber;

an upper chamber located above the purification chamber receiving air from the purification chamber, wherein the purification chamber housing and the plurality of baffles prevent the ultraviolet radiation from entering the upper chamber and wherein the air from the purification chamber exits through a discharge grille adjacent to the upper chamber; and an outer housing comprising the discharge grille and enclosing the filtration apparatus, the upper chamber, the blower, and the purification chamber, wherein the discharge grille is angled away from an intake grille oriented toward an external setting and sloped relative to a bottom side of the outer housing.

8. The apparatus of claim 7, further comprising a bipolar ionization unit positioned within the purification chamber proximate to the blower, the bipolar ionization unit configured to cause a further treatment of the air.

9. The apparatus of claim 7, wherein the filtration apparatus is positioned between the external setting and the blower in a path of the air from the external setting to the inlet of the blower.

10. The apparatus of claim 7, wherein the ultraviolet lamp is positioned within the purification chamber between the blower and the external setting in a path of the air from the outlet of the blower to the external setting.

11. The apparatus of claim 7, further comprising a control module configured to control an operation of the blower.

12. The apparatus of claim 7, wherein the blower comprises a centrifugal blower, a high-speed blower, an axial fan, a backwards inclined fan, or a plug fan.

13. The apparatus of claim 7, wherein the filtration apparatus comprises a pre-filter and a filter, the filter comprising a high-efficiency particulate air (HEPA) filter, and the pre-filter comprising a filter having a lower efficiency compared to the HEPA filter.

* * * * *